United States Patent [19]

Reissenweber et al.

[11] Patent Number: 5,677,452

[45] Date of Patent: Oct. 14, 1997

[54] PROCESS FOR THE MANUFACTURE OF 5-DICHLOROACETYL-3,3,6-TRIMETHYL-9-OXO-1,5-DIAZABICYCLO[4.3.0] NONANE

[75] Inventors: Gernot Reissenweber, Boehl-Iggelheim; Winfried Richarz, Stockstadt; Knut Koob, Mutterstadt, all of Germany

[73] Assignee: BASF Aktiengesellschaft, Ludwigshafen, Germany

[21] Appl. No.: 736,438

[22] Filed: Oct. 24, 1996

Related U.S. Application Data

[63] Continuation of Ser. No. 343,570, filed as PCT/EP93/01234, May 18, 1993, abandoned.

[30] Foreign Application Priority Data

May 29, 1992 [DE] Germany .................. 42 17 846.0

[51] Int. Cl.⁶ .................................. C07D 239/00
[52] U.S. Cl. ............................................ 544/282
[58] Field of Search .............................. 544/282

[56] References Cited

U.S. PATENT DOCUMENTS

| | | | |
|---|---|---|---|
| 4,448,960 | 5/1984 | Rohr et al. | 544/282 |
| 4,565,565 | 1/1986 | Rohr et al. | 544/282 |
| 4,995,899 | 2/1991 | Scholz et al. | 544/282 |
| 5,254,564 | 10/1993 | Vecchietti et al. | 514/307 |

FOREIGN PATENT DOCUMENTS

| | | |
|---|---|---|
| 1278695 | 1/1986 | Canada . |
| 031 042 | 11/1980 | European Pat. Off. . |
| 190 105 | 1/1986 | European Pat. Off. . |
| 229 649 | 1/1987 | European Pat. Off. . |
| 1 802 468 | 10/1968 | Germany . |

OTHER PUBLICATIONS

Characteristics of Free Radicals, 867–875, 1967.

Houben–Weyl, Methoden der Organischen Chemie, vol. 11/2, 4th Edt. Georg Thieme Verlag 1958, pp. 12 and 13 (Schotten–Baumann acylation).

*Primary Examiner*—Matthew V. Grumbling
*Attorney, Agent, or Firm*—Keil & Weinkauf

[57] ABSTRACT

The manufacture of 5-dichloroacetyl-3,3,6-trimethyl-9-oxo-1,5-diazabicyclo[4.3.0]-nonane I by the reaction of 3,3,6-trimethyl-9-oxo-1,5-diaza-bicyclo[4.3.0]nonane II with dichloroacetyl chloride in the presence of a solvent and a base, wherein a) this reaction is carried out in a two-phase system comprising a virtually water-insoluble organic solvent and water, and sodium or potassium hydroxide acting as the base is metered in at a rate corresponding to the rate of consumption of the dichloroacetyl chloride such that the aqueous phase exhibits a pH of from 7 to 9, and b) the resulting product is separated.

10 Claims, No Drawings

PROCESS FOR THE MANUFACTURE OF 5-DICHLOROACETYL-3,3,6-TRIMETHYL-9-OXO-1,5-DIAZABICYCLO[4.3.0] NONANE

This application is a continuation of application Ser. No. 08/343,570, filed as PCT/EP93/01234 May 18, 1993 now abandoned.

The present invention relates to an improved process for the preparation of 5-dichloroacetyl-3,3,6-trimethyl-9-oxo-1,5-diazabicyclo[4.3.0]nonane of the formula I

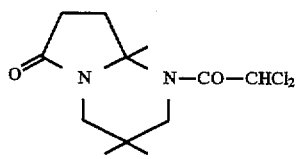

by the reaction of 3,3,6-trimethyl-9-oxo-1,5-diaza-bicyclo[4.3.0]nonane II

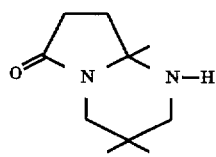

with dichloroacetyl chloride in the presence of a solvent and a base.

EP-A 031,042, EP-A 190,105 and EP-A 229,649 disclose that 5-dichloroacetyl-3,3,6-trimethyl-9-oxo-1,5-diazabicyclo[4.3.0]nonane (I) can be obtained by the reaction of 3,3,6-trimethyl-9-oxo-1,5-diazabicyclo[4.3.0]nonane (II) with dichloroacetyl chloride in the presence of a hydrogen chloride-binding agent, toluene being one suitable solvent or diluent for this purpose.

According to EP-A 229,649, suitable hydrogen chloride-binding agents are inter alia aqueous solutions of alkali-metall hydroxides. In the only process example in EP-A 031,042 and in example 4 of EP-A 229,649, however, only the reaction technique carried out in toluene using triethylamine as hydrogen chloride-binding agent is described in detail. In these cases, on completion of the reaction, it is first necessary to separate solid triethylamine hydrochloride, after which (I) is separated and subsequently recrystallized by evaporating off the solvent. This reaction technique involving double separation of solids (salt and product) and subsequent separate purification of the product is elaborate as regards both process engineering and energy.

It was thus the object of the invention to provide a simple and industrially economical process for the preparation of I, in which the I produced is as pure as possible.

Accordingly, we have found a process for the preparation of 5-dichloroacetyl-3,3,6-trimethyl-9-oxo-1,5-diazabicyclo[4.3.0]-nonane I, wherein a) the reaction of II with dichloroacetyl chloride is carried out in a two-phase system comprising a virtually water-insoluble organic solvent and water, and sodium or potassium hydroxide acting as base is metered in at a rate corresponding to the rate of consumption of the dichloroacetyl chloride, such that the aqueous phase exhibits a pH of from 7 to 9, and b) the resulting solid product is separated.

Suitable organic solvents are primarily aromatic hydrocarbons, such as benzene and preferably mono- or poly-alkylated benzenes containing 7 to 12 carbon atoms, such as toluene, ethylbenzene, dimethylbenzenes, and xylenes.

Particularly good results are achieved by a two-phase system comprising toluene and water.

Generally, the ratio of water to organic solvent is between 1:3 and 2:1, the quantity of organic solvent preferably being between 0.5 and 1.5 liters per mole of compound II.

The sodium or potassium hydroxide, preferably sodium hydroxide, is usually used in the form of an aqueous solution.

Particularly favorable results are achieved by introducing dichloroacetyl chloride and sodium or potassium hydroxide concurrently but separately to the two-phase system comprising II in toluene and water, the quantity of base being such as to keep the pH of the aqueous phase, throughout the reaction, between approximately 7 and 9, in particular between 7.5 and 8.8, preferably between 8.2 and 8.6. As far as is known to date, the yield of I falls steeply as the pH progressively exceeds 9.

In order to achieve as high a yield as possible, dichloroacetyl chloride and II are used in approximately equimolar amounts; however, it is advantageous to operate with an excess of dichloroacetyl chloride of up to approximately 50 mol %, in particular with an excess of from 10 to 20 mol %, based on the quantity of II.

Generally speaking, a reaction temperature between 0° and 80° C., in particular between 20° and 60° C., preferably between 30° and 55° C., is adequate.

Special conditions regarding the pressure are not necessary; normally the reaction is therefore carried out at atmospheric pressure. Lower or higher pressures are possible but do not normally create any advantages.

The product I formed during the reaction precipitates from the reaction mixture as solid material. It is separated in the usual manner, for example, by filtration or centrifugation.

Following washing with water, the product obtained has such a high degree of purity that further purifying operations are unnecessary.

A particularly advantageous embodiment of the process consists in manufacturing the starting product II by a process such as is known pe se from DE-A 1,802,468 [cf also *Angew. Chem.* 81, 34 (1969) and the literature cited therein] from 4-oxopentanoic acid and neopentylamine, and to subject it to the process of the invention without isolation from the reaction mixture using the same or a different reaction vessel.

An advantageous procedure consists in allowing 4-oxopentanoic acid and neopentylamine to react in the desired organic solvent with constant removal of the water thus formed, e.g., by means of azeotropic distillation, until no more water is formed and the boiling point of the reaction mixture remains constant. The addition of water or water separated during the reaction then provides the two-phase solvent mixture required for further reaction.

In this embodiment, calculation of the quantity of dichloroacetyl chloride required for the conversion of II to I is advantageously based on the quantity of 4-oxopentanoic acid rather than on that of II.

For quantitative conversion of 4-oxopentanoic acid and neopentane diamine, at least equimolar amounts or a slight excess of one or the other component of up to approximately 5 mol % are necessary. Larger excesses of one of the starting materials are possible but do not create any advantages.

The quantity of organic solvent used should be such that the starting materials are completely dissolved. Normally, it is sufficient to use the solvent in an amount equal to from five to ten times that of one of the educts.

Generally, the reaction temperature for the manufacture of II lies between 40° and 140° C. and preferably between 60° C. and the boiling temperature of the solvent.

Preferably, the reaction is carried out at atmospheric pressure or under the autogenous pressure of the solvent used.

The process of the invention represents a special embodiment of the Schotten-Baumann acylation (cf, e.g., Houben-Weyl, *Methoden der Organischen Chemie*, Vol. 11/2, 4th Edition, Georg Thieme Verlag 1958, page 12 (13th line from the bottom) and page 13). It makes it possible to manufacture I in a simple manner and in a purity exceeding 97%, the yield being very high.

5-Dichloroacetyl-3,3,6-trimethyl-9-oxo-1,5-diazabicyclo[4.3.0]nonane I is used in plant protection, for example, particularly as an antidote for improving the tolerance of herbicides, e.g. those in the class comprising the acetanilides, with regard to cultivated plants.

EXAMPLES

Preliminary stage (manufacture of 3,3,6-trimethyl-9-oxo-1,5-diaza-bicyclol[4.3.0]nonane (II)

119.6 g (1 mol) of levulinic acid (97% pure) in 600 mL of toluene were heated at from 105° to 110° C. To this mixture there were added dropwise, with constant removal, by distillation, of the resulting water of reaction, 103.0 g (1 mol) of neopentylamine (99% pure), which was kept liquid by the addition of 5 wt % of toluene. When the addition of the neopentylamine was near completion, the reaction temperature was raised to ca 115° C. This temperature was maintained until the theoretical quantity of water (=36 g) had distilled off and the transition temperature of the distillate was 110° C. The reaction mixture was then cooled to about 50° C.

Manufacture of I
(invention)

To the reaction mixture obtained from the preliminary stage there were added 800 mL of water and then 25 wt % strength caustic soda until the aqueous phase had a pH of 8.4. To this two-phase mixture there were added dropwise, at from 40° to 45° C. over a period of 1 h, 173.1 g (1.15 mol) of dichloroacetyl chloride (98% pure), the pH of the aqueous phase being kept constant by the addition of 25 wt % strength caustic soda (in all: 21.60 g). Finally, the mixture of products was stirred for a further 30 min and then cooled to from 20° to 25° C. The solid product was separated, and washed with ca 500 mL of water. Mp: 171° C.

Yield: 92.7%. Purity: 98.4% (as determined by HPLC analysis).

Comparative Example A

To the reaction mixture obtained from the preliminary stage there were added, at from 40° to 45° C. over a period of one hour, 173.1 g (1.15 mol) of dichloroacetyl chloride (98% pure) and 21.60 g of a 25 wt % strength caustic soda solution.

Finally, the mixture of products was stirred for a further 30 min and then cooled to from 20° to 25° C. The solid product was separated and washed with ca 500 mL of water.

Yield: 81.8%. Purity: 89.9% (as determined by HPLC analysis).

Comprative Example B

To the reaction mixture obtained from the preliminary stage there were initially added 21.60 g of a 25 wt % strength caustic soda solution. To this mixture there were then added dropwise, at from 40° to 45° C. over a period of 1 h, 173.1 g (1.15 mol) of dichloroacetyl chloride (98% pure).

Finally, the mixture of products was stirred for a further 30 min and then cooled to from 20° to 25° C. The solid product was separated and washed with ca 500 mL of water.

Yield: 82.9%. Purity: 94.1% (as determined by HPLC analysis).

We claim:

1. A process for the preparation of 5-dichloroacetyl-3,3,6-trimethyl-9-oxo-1,5-diazabicyclo[4.3.0]-nonane (I)

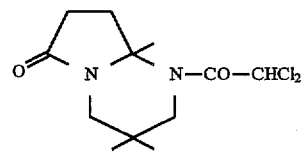

by the reaction of 3,3,6-trimethyl-9-oxo-1,5-diaza-bicyclo[4.3.0]nonane II

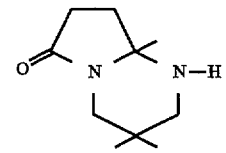

with dichloroacetyl chloride in the presence of a solvent and a base, wherein a) this reaction is carried out in a two-phase system comprising a virtually water-insoluble organic solvent and water, and sodium or potassium hydroxide acting as base is metered in at a rate corresponding to the rate of consumption of the dichloroacetyl chloride, such that the aqueous phase exhibits a pH of from 7 to 9, and b) the resulting solid product is separated.

2. A process as defined in claim 1, wherein the starting point is a mixture of 3,3,6-trimethyl-9-oxo-1,5-diazabicyclo[4.3.0]nonane II in a virtually water-insoluble organic solvent, obtained when II is prepared from 4-oxopentanoic acid and neopentane diamine with constant removal of the water formed.

3. A process as defined in claim 1, wherein the organic solvent used is a mono- or poly-alkylated benzene containing 7 to 12 carbon atoms.

4. A process as defined in claim 1, wherein the reaction is carried out at a pH of from 7.5 to 8.8.

5. A process as defined in claim 1, wherein the reaction is carried out at a temperature between 20° and 60° C.

6. A process as defined in claim 2, wherein the organic solvent used is a mono- or polyalkylated benzene having from 7 to 12 carbon atoms.

7. A process as defined in claim 2, wherein the reaction is carried out at a pH of from 7.5 to 8.8.

8. A process as defined in claim 2, wherein the reaction is carried out at a temperature between 20° and 60° C.

9. A process as in claim 5 wherein the reaction is carried out at a temperature between 30° and 55° C.

10. A process as in claim 8 wherein the reaction is carried out at a temperature between 30° and 55° C.

* * * * *